United States Patent [19]

Kawasaki

[11] Patent Number: 4,599,311

[45] Date of Patent: Jul. 8, 1986

[54] GLYCOLYTIC PROMOTERS FOR REGULATED PROTEIN EXPRESSION: PROTEASE INHIBITOR

[76] Inventor: Glenn H. Kawasaki, 1547 - 16th Ave. East, Seattle, Wash. 98112

[21] Appl. No.: 408,099

[22] Filed: Aug. 13, 1982

[51] Int. Cl.[4] .................. C12P 21/04; C12P 21/02; C12N 1/18; C12N 1/00
[52] U.S. Cl. .................................. 435/71; 435/68; 435/70; 435/256; 435/317; 935/11; 935/12; 935/28; 935/37; 935/6
[58] Field of Search .................. 435/172, 68, 70, 71, 435/317, 256; 536/27

[56] References Cited

PUBLICATIONS

Hitzeman et al, The Journal of Biological Chemistry, vol. 255, No. 24, pp. 12073–12080, Dec. 25, 1980.
Tuite et al, The EMBO Journal, vol. 1, No. 5, pp. 603–608 (1982).
Hitzeman et al, Nature, vol. 293, pp. 717–722, Oct. 29, 1981.
Strathern et al, The Molecular Biology of the Yeast Saccharomyces, Metabolism and Gene Expression, pp. 1–37, 590, 599 & 604 (1982).
Woo et al, Miami Winter Symposia, vol. 19, From Gene to Protein: Translation Into Biotechnology, p. 579 (Jan. 1982).
Dobson et al, Nucleic Acids Research, vol. 10, No. 8, pp. 2625–2637, Apr. 24, 1982.

*Primary Examiner*—Alvin E. Tanenholtz
*Attorney, Agent, or Firm*—Flehr, Hohbach, Test, Albritton & Herbert

[57] ABSTRACT

Promoters associated with expression of specific enzymes in the glycolytic pathway are used for expression of alien DNA, particularly yeast promoters known to provide high enzyme levels of enzymes in the glycolytic pathway are employed for expressing a mammalian protein, such as $a_1$-antitrypsin. The promoters include promoters involved in expression of pyruvate kinase, triose phosphate isomerase, phosphoglucose isomerase, phosphoglycerate mutase, hexokinase 1, hexokinase 2, glucokinase, phosphofructokinase, and aldolase, as well as the glycolytic regulation gene. Particularly, the glycolytic regulation gene can be used in conjuction with promoters in the glycolytic pathway for regulated production of desired proteins.

17 Claims, No Drawings

GLYCOLYTIC PROMOTERS FOR REGULATED PROTEIN EXPRESSION: PROTEASE INHIBITOR

BACKGROUND OF THE INVENTION

1. Field of the Invention

The ability to obtain expression of foreign, i.e., exogenous, DNA in unicellular microorganisms provided the opportunity to conveniently prepare long polypeptide chains of interest. Almost immediately, varied polypeptides, such as the small hormone somatostatin and more sophisticated polypeptides, such as insulin, interferons, thymosin and a variety of vaccines having capsid proteins, were prepared and reported in the literature. For the most part, the initial work was performed in the bacterium E. coli which had been the subject of intensive study because scientists were familiar with many aspects of its genetic structure and properties. Initial attention was therefore directed to producing foreign proteins in E. coli. Once the ability to employ E. coli as a host was established, the limitations and disadvantages of employing E. coli encouraged the use of other hosts.

One host which appeared to be particularly attractive because it lacked many of the shortcomings of E. coli was yeast. However, yeast is a eukaryote and, therefore, has a more sophisticated genetic system. Furthermore, less is known about the yeast genome than is known about E. coli. In order to use yeast as a host for the production of proteins foreign to yeast, a number of discoveries are required, and new materials must be made available.

Initially, a replication system was required which provided stability in yeast, either as an extrachromosomal element or by integration into the yeast chromosome. In addition, the regulatory functions concerned with transcription and expression had to be developed in order to allow for expression of the desired protein. There was also the uncertainty whether foreign DNA sequences would be transcribed and translated and, if expressed, whether the resulting polypeptides would survive in the yeast cell. Also remaining to be determined was the effect of the foreign proteins on the viability of the yeast cell, such as the effect of recombinant DNA (RDNA) on mitosis, sporulation and vegetative growth.

There have, therefore, been substantial efforts to develop novel RDNA systems in yeast, which will allow for regulated expression of a protein of interest, as well as highly efficient production of such proteins.

2. Description of the Prior Art

Hitzeman et al., J. Biol. Chem. (1980) 255:12073–12080 describe a plasmid having a yeast 3-phosphoglycerate kinase (PGK) gene and accompanying regulatory signals capable of expression in yeast. Other references of interest include Clifton, et al., Genetics (1978) 88:1–11; Clark and Carbon, Cell (1976) 9:91–99; Thomson, Gene (1977) 1:347–356; Holland and Holland, J. Biol. Chem. (1979) 254:5466–5474; Holland and Holland, ibid. (1979) 254:9830–9845; Nasmyth and Reed, Proc. Nat. Acad. Sci. (1980) 77:2119–2123; Broach, et al., Gene (1979) 8:121–133; and Williamson, et al., Nature (1980) 283:214–216.

SUMMARY OF THE INVENTION

Novel yeast promoters are provided which control the transcription of genes in the glycolytic pathway and which find use in the regulated production of proteins foreign to the yeast. Promoters of particular interest include the promoters for triose phosphate isomerase, pyruvate kinase, phosphoglucose isomerase, phosphoglycerate mutase, hexokinase 1, hexokinase 2, glucokinase, phosphofructokinase, and aldolase, as well as the glycolytic regulatory gene. The protease inhibitor, mammalian $\alpha_1$-antitrypsin, is expressed using the promoter for triose phosphate isomerase.

DESCRIPTION OF THE SPECIFIC EMBODIMENTS

Methods and compositions are provided for regulated efficient expression of alien or foreign DNA in a yeast host. (Alien or foreign DNA is DNA not naturally occurring in the wild type particularly from a different species and which does not normally exchange genetic information with the host.) Novel promoters are employed which are involved in the glycolytic pathway and provide for high levels of protein production, so that a substantial proportion of the total protein produced by the yeast cells can be dedicated to the protein of interest. In addition, regulatory mechanisms associated with regulation of production of the glycolytic enzymes are achieved, so that production of the desired products may be modulated. Furthermore, viable cells can be maintained to enhance the efficiency and amount of expression.

The promoters of interest are particularly those promoters involved with expression of triose phosphate isomerase, pyruvate kinase, phosphoglucose isomerase, phosphoglycerate mutase, hexokinase 1, hexokinase 2, glucokinase, phosphofructokinase, and aldolase, which are controlled by the glycolytic regulation gene GCR1. The genes of the glycolytic pathway include hexokinase 1 and 2 (HXK1,2); phosphoglucose isomerase (PGI), triose phosphate isomerase (TPI); phosphoglycerate kinase (PGK), phosphoglycerate mutase (GPM), pyruvate kinase (PYK); phosphofructokinase (PFK), enolase (ENO); fructose 1,6-diphosphate aldolase (FDA); glyceraldehyde 3-phosphate dehydrogenase (PGK); and glycolysis regulation protein (GCR).

The promoters may be obtained by employing a gene bank having large fragments of yeast DNA. By introducing the fragments into appropriate vectors, particularly shuttle vectors having replicons for prokaryotes and yeast, one can readily amplify and clone the yeast DNA in a bacterium and then introduce the yeast DNA into mutant yeast cells for complementation. In this manner, yeast fragments can be identified which complement auxotrophic lesions or mutations in a yeast host.

Of particular interest, is where the host is auxotrophic in both the glycolytic pathway step of interest and a separate biochemical pathway, which is complemented by a marker in the vector. Once having established a DNA segment having the desired gene, one may reclone by various techniques to shorten the DNA segment and provide for a segment which is primarily the gene of interest in conjunction with its regulatory signals for transcription and expression.

In order to retain the promoter, it is essential that the initiator methionine be determined and this codon be used for developing the strategy for introducing the alien DNA downstream from the promoter. Various techniques can be employed for providing a site for introduction of the alien DNA so as to be under the regulatory control of the promoter in the glycolytic pathway.

Where a restriction site is conveniently adjacent to the initiator methionine codon, the glycolytic gene may be cleaved at that site and the DNA chewed back with Bal31 for varying periods of time, so as to chew into or past the initiator methionine codon or retain the initiator methionine codon.

Where there is no convenient restriction site, other splicing techniques such as primer repair may be employed. Also, by employing in vitro mutagenesis, one can introduce a restriction site adjacent the initiator methionine, which encodes for the initial amino acids of the desired protein. In each instance, a linearized DNA segment is obtained having the intact promoter for the glycolytic product and normally includes other DNA sequences, such as an intact replicon, one or more markers, and the like.

Exemplary of the above procedure is the development of a vector having the promoter for the TPI1 gene. An exemplary vector CV13 having the replicons or replication systems from pBR322 and 2μ-plasmid of yeast, as well as the LEU2 gene was employed for insertion of a yeast fragment which was shown to have the TPI1 gene. This was achieved by employing double selection with a mutant yeast which was leu$^-$, tpi$^-$. The TPI1 gene was found to have a unique KpnI site. The vector was cleaved at the KpnI site and then treated with the double stranded exonuclease Bal31 for varying times to chew back the DNA to about the f-met codon. Linkers were then inserted providing desired restriction sites. Alien DNA could then be inserted providing a sequence having a f-met codon in the appropriate position for initiation. Alternatively, the foreign DNA can be expressed using the f-met codon of the TPI1 gene.

Similar procedures can be performed with the other subject glycolytic genes in order to provide the promoters associated with those genes. The PYK sequence has a convenient XbaI site for restriction, where the few additional bases may be removed, if required, using Bal31 for a short period of time to chew to or through the methionine codon. Of particular interest is the use of the GCR promoter to control the expression of the other genes involved in the glycolytic pathway. By employing the GCR gene, in conjunction with other glycolytic promoters regulating expression of alien DNA, one can turn on and off the other promoters, so as to regulate the expression of the alien DNA. Thus, one can allow vegetative growth to proceed until a desired cell density is achieved, before permitting production of the desired polypeptide.

By employing appropriate auxotrophs, one can further regulate the expression of the polypeptides of interest in choosing the appropriate nutrient medium. Where the chosen promoter is repressed by the particular nutrient because of a metabolic block, a change in the nature of the nutrient can induce expression. Furthermore, the activity of a number of promoters in the glycolytic pathway can be affected by the repression or activation of expression by the GCR gene or other regulatory controls. Also, the GCR regulatory signals can be used to titrate the polypeptide functioning as the regulator for expression of GCR. By having vectors whose copy number can be controlled, one can vary the activity of the wild type GCR gene.

In order to obtain expression, an extrachromosomal element construct will be prepared having a number of sequences defining different functions. One function is the replication system, which forms part of a vector. Another function is a promoter by itself or in conjunction with the alien DNA. Other functions include initiators and terminators of expression. Also, there will be selectable markers.

In developing an appropriate vector, while not necessary, it will be common to have both a replication system for yeast and a replication system for a prokaryote (a shuttle vector). The replication system for yeast may be one which provides for stable maintenance of an extrachromosomal element or one which provides a sufficient lifetime for the DNA in the host, that there is an acceptable probability of integration of the DNA into the host. Integration can be greatly aided by providing for a sequence homologous to the host DNA, so as to provide for recombination. Generally, the homologous sequence will be at least about 800bp usually not more than about 2000bp. Therefore, either integration or an autonomous replication system, such as the use of the ARS1 gene, may be employed to provide for the maintenance of the alien DNA in the yeast host. The replication system which is chosen should provide for a reasonable copy number usually greater than 1, preferably greater than 5. A wide variety of replication systems are available on a wide variety of prokaryotic vectors, such as pBR322, pACYC184, pSC101, pMB9, etc. Alternatively, one or more copies of the DNA construct can be integrated into the host chromosome. The replication systems may also be conditionally regulated, usually being temperature sensitive so that replication can be turned on and off by varying the temperature.

In addition to the replication system, there will also be one or more selectable markers, there usually being at least one marker in addition to the alien DNA, which may serve as a marker. Conventional markers include biocidal markers providing antibiotic resistance and those providing resistance to toxins and heavy metal. Also useful is employing an auxotrophic host and providing prototrophy by complementation. In addition to the conventional selection systems just described, the glycolytic genes of the present invention are particularly desirable markers since they can provide for selection, using sugars as selective substrates, in appropriate mutant host strains.

Other genes may also be inserted into the extrachromosomal element for a variety of purposes. Where integration is desirable in the genome of the host, a homologous sequence for a particular region of the host genome may be included in the extrachromosomal element. Where amplification of one or more sequences is desired, genes known to provide such amplification, such as dihydrofolate reductase genes, which respond to methotrexate stress or metallothionein genes, which respond to heavy metal stress, may be included in the extrachromosomal element, flanked by the DNA regions to be reiterated. Other regulatory signals may also be included, such as centromeres, autonomously replicating segments, etc.

In order to isolate the promoters of interest, clones can be made of yeast chromosomal DNA by random digestion or mechanical shearing of the yeast genome. The presence of the desired gene is then determined by introducing a homogeneous clone of a yeast fragment into an auxotrophic host for complementation. Desirably, the cloning vehicle may have another gene which allows for an additional basis for selection, so that double selection techniques can be used. The mutants are substantially incapable of growing on limited nutrient medium, so that one can select for the presence of the desired glycolytic gene by the choice of medium. After isolating the yeast fragment having the desired gene, the fragment may be subcloned so as to remove superfluous DNA flanking regions and provide for a fragment which is more easily manipulated. The smaller fragment containing the desired gene, of a size less than about 500 base pairs may then be further cloned, restriction mapped and sequenced, so as to provide a useful source for the desired promoters and insertion of the alien DNA. Also, as indicated, the promoters in themselves may be useful, in acting as a titrater for repressor or activator, where it is desirable to modulate the production of a particular enzyme in the yeast host.

The alien DNA may be from any source, either naturally occurring or synthetic, either prokaryotic or eukaryotic. Of particular interest are mammalian genes which express a poly(amino acid), that is, polypeptide or protein which has physiological activity. To varying degrees, poly(amino acids) prepared in yeast may be modified by glycosylation, where the glycosylation may not occur or may occur at different sites from the naturally occurring mammalian polypeptide and/or in different degrees with different saccharides. It is therefore of great interest to be able to prepare polypeptides which are different from the naturally occurring polypeptide by the degree and manner of glycosylation and in many instances may differ in one or more ways as to the amino acid sequences, where there may be deletions of one or more amino acids or substitutions of one or more amino acids. Mammalian genes may come from a wide variety of mammalian sources, such as domestic animals (e.g. bovine, porcine, ovine and equine) and primates e.g. humans and monkeys.

As exemplary of the use of the subject promoters in preparing an active polypeptide composition, as well as being of particular interest for a variety of purposes, a protease inhibitor is described and made. The protease inhibitor has the same or substantially the same amino acid sequence of human $\alpha_1$-antitrypsin and is capable of inhibiting a number of proteolytic enzymes. The human $\alpha_1$-antitrypsin gene appears to reside within a 9.6 kb EcoRI DNA fragment in the human genome. The mature mRNA appears to have about 1400 nucleotides. One human $\alpha_1$-antitrypsin cDNA has the following sequence, although other naturally-occurring forms (polymorphisms) are known.

```
                                                        5'  GGGGGGGGGGGGGGAGTGAATCGACA
        -24                                    -20                                    -10                                               -1
        Met Pro Ser Ser Val Ser Trp Gly Ile Leu Leu Ala Gly Leu Cys Cys Leu Val Pro Val Ser Leu Ala
        ATG CCG TCT TCT GTG TCT TGG GGC ATC CTC CTG GCT GGC CTG TGC TGC CTG GTC CCT GTC TCC CTG GCT
                   10                            20                            30                            40                   50                            60                            70
        +1
         1                                           10                                           20
        Glu Asp Pro Gln Gly Asp Ala Ala Gln Lys Thr Asp Thr Ser His His Asp Gln Asp His Pro Thr Phe Asn
        GAG GAT CCC CAG GGA GAT GCT GCC CAG AAG ACA GAT ACA TCC CAC CAT GAT CAG GAT CAC CCA ACC TTC AAC
                   80                            90                            100                           110                           120                           130                           140
                                      30                                           40
        Lys Ile Thr Pro Asn Leu Ala Glu Phe Ala Phe Ser Leu Tyr Arg Gln Leu Ala His Gln Ser Asn Ser Thr
        AAG ATC ACC CCC AAC TTG GCT GAG TTC GCC TTC TCA GCC CTA CGG CAG CTG GCA CAC CAG TCC AAC AGC ACC
                   150                           160                           170                           180                           190                           200                           210
                   50                                           60                                           70
        Asn Ile Phe Phe Ser Pro Val Ser Ile Ala Thr Ala Phe Ala Met Leu Ser Leu Gly Thr Lys Ala Asp Thr
        AAT ATC TTC TTC TCT CCC AGT GAG CAT CGC TAC AGC CCT TTG CAA TGC TCT CCC TGG GAC CAA GGC TGA CAC T
                   220                           230                           240                           250                           260                           270                           280
        His Asp Glu Ile Leu Glu Gly Leu Asn Phe Asn Leu Thr Glu Ile Pro Glu Ala Gln Ile His Glu Gly Phe
        CAC GAT GAA ATC CTG GAG GGC CTG AAT TTC AAC CTC ACG GAG ATT CCG GAG GCT CAG ATC CAT GAA GGC TTC
                   290                           300                           310                           320                           330                           340                           350
                                      80                                           90                                           100
        Gln Glu Leu Leu Arg Thr Leu Asn Gln Pro Asp Ser Gln Leu Gln Leu Thr Thr Gly Asn Gly Leu Phe Leu
        CAG GAA CTC CTC CGT ACC CTC AAC CAG CCA GAC AGC CAG CTC CAG CTG ACC ACC GGC AAT GGC CTG TTC CTC
                   360                           370                           380                           390                           400                           410                           420
                                              110                                          120
        Ser Glu Gly Leu Lys Leu Val Asp Lys Phe Leu Glu Asp Val Lys Lys Leu Tyr His Ser Glu Ala Phe Thr
        AGC GAG GGC CTG AAG CTA GTG GAT AAA TTT TTG GAG GAT GTT AAA AAG TTG TAC CAC TCA GAA GCC TTC ACT
                   430                           440                           450                           460                           470                           480                           490
                                             130                                          140
        Val Asn Phe Gly Asp Thr Glu Glu Ala Lys Lys Gln Ile Asn Asp Tyr Val Glu Lys Gly Thr Gln Gly Lys
        GTC AAC TTC GGG GAC ACC GAA GAG GCC AAG AAA CAG ATC AAC GAT TAC GTG GAG AAG GGT ACT CAA GGG AAA
                   500                           510                           520                           530                           540                           550                           560
                                      150                                          160                                          170
        Ile Val Asp Leu Val Lys Glu Leu Asp Arg Asp Thr Val Phe Ala Leu Val Asn Tyr Ile Phe Phe Lys Gly
        ATT GTG GAT TTG GTC AAG GAG CTT GAC AGA GAC ACA GTT TTT GCT CTC GTG AAT TAC ATC TTC TTT AAA GGC
                   570                           580                           590                           600                           610                           620                           630                           640
                                      180                                          190
        Lys Trp Glu Arg Pro Phe Glu Val Lys Asp Thr Glu Glu Glu Asp Phe His Val Asp Gln Val Thr Thr Val
        AAA TGG GAG AGA CCC TTT GAA GTC AAG GAC ACC GAG GAA GAG GAC TTC CAC GTG GAC CAG GTG ACC ACC GTG
                   650                           660                           670                           680                           690                           700                           710                           720
                              200                                          210
```

```
     220                                              230                                          240
Lys Val Pro Met Met Lys Arg Leu Gly Met Phe Asn Ile Gln His Cys Lys Lys Leu Ser Ser Trp Val Leu
AAG GTG CCT ATG ATG AAG CGT TTA GGC ATG TTT AAC ATC CAG CAT TGT AAG AAG CTG TCC AGC TGG GTG CTG
                    730                                 750                                 780                              790
                                            250                                             260
Leu Met Lys Tyr Leu Gly Asn Ala Thr Ala Ile Phe Phe Leu Pro Asp Glu Gly Lys Leu Gln His Leu Glu
CTG ATG AAA TAC CTG GGC AAT GCC ACC GCC ATC TTC TTC CTG CCT GAT GAG GGG AAA CTA CAG CAC CTG GAA
 800                            810                             830                            850           860

270                                             280
Asn Glu Leu Thr His Asp Ile Ile Thr Lys Phe Leu Glu Asn Glu Asp Arg Arg Ser Ala Ser Leu His Leu
AAT GAA CTC ACC CAC GAT ATC ATC ACC AAG TTC CTG GAA AAT GAA GAC AGA AGG TCT GCC AGC TTA CAT TTA
                   870    880                        900                    910        920            930

290                                            300                         310
Pro Lys Leu Ser Ile Thr Gly Thr Tyr Asp Leu Lys Ser Val Leu Gly Gln Leu Gly Ile Thr Lys Val Phe
CCC AAA CTG TCC ATT ACT GGA ACC TAT GAT CTG AAG AGC GTC CTA GGT CAA CTG GGC ATC ACT AAG GTC TTC
       940            950              960                 980                 990            1000

320                                     330
Ser Asn Gly Ala Asp Leu Ser Gly Val Thr Glu Glu Ala Pro Leu Lys Leu Ser Lys Ala Val His Lys Ala
AGC AAT GGG GCT GAC CTC TCC GGG GTC ACA GAG GAG GCA CCC CTG AAG CTC TCC AAG GCC GTG CAT AAG GCT
 1010          1020                  1030                1050                  1060             1080

340                                           350                                360
Val Leu Thr Ile Asp Glu Lys Gly Thr Glu Ala Ala Gly Ala Met Phe Leu Glu Ala Ile Pro Met Ser Ile
GTG CTG ACC ATC GAC GAG AAA GGG ACT GAA GCT GCT GGG GCC ATG TTT TTA GAG GCC ATA CCC ATG TCT ATC
                1090                    1100                  1120                    1140

370                                            380
Arg Pro Glu Val Lys Phe Asn Lys Pro Phe Val Phe Leu Met Ile Glu Gln Asn Thr Lys Ser Pro Leu Phe
GGC CCC GAG GTC AAG TTC AAC AAA CCC TTT GTC TTC TTA ATG ATT GAA CAA AAT ACC AAG TCT CCC CTC TTC
          1160                  1170                  1190                 1200            1220

390              394
Met Gly Lys Val Val Asn Pro Thr Gln Lys STOP
ATG GGG AAA AGT GGT GAA TCC CCA AAA TAA CTG CCT CTC TCG CCT CTC AAC CCC CCC CCC       3'
           1230               1240                           1250
```

The human $\alpha_1$-AT has a BamHI restriction site which allows the cutting of the gene with the removal of information for a single glutamic acid from the mature protein. Various schemes can be employed for introducing the human $\alpha_1$-AT gene adjacent the glycolytic promoter to be under the regulation of the promoter. Where the promoter does not have a convenient restriction site near the f-met codon, the glycolytic gene may be cleaved and chewed back to the promoter with Bal31. A linker may then be introduced downstream from the promoter to provide a convenient cohesive end or flush end for joining to the human $\alpha_1$-AT gene. The linker can also provide one or more codons for amino acids at the N-terminus of the $\alpha_1$-AT gene, which may be the same or different from the naturally occurring amino acids.

The gene for human $\alpha_1$-AT may then be inserted into the extrachromosomal element downstream from the glycolytic promoter, where an f-met codon is provided for initiation of expression of the human $\alpha_1$-AT.

The resulting extrachromosomal element containing the human $\alpha_1$-AT gene may then be introduced into a yeast host, particularly an auxotrophic host and the yeast host grown for expression of a polypeptide having $\alpha_1$-antitrypsin activity. The resulting polypeptide differs from the naturally occurring human $\alpha_1$-AT in its degree of glycosylation.

The $\alpha_1$-antitrypsin can be used as an antigen for production of polyclonal and monoclonal antibodies to human $\alpha_1$-AT, for introduction into a host having a deficiency of $\alpha_1$-AT, or for modulating proteolytic activity in a mammalian host. In particular, the $\alpha_1$-antitrypsin can be administered to humans to replace $\alpha_1$-antitrypsin which has been inactivated (oxydized) by tobacco and other smoke.

The following examples are offered by way of illustration and not by way of limitation.

EXPERIMENTAL

Materials and Methods

Strains.

Isogenic strains carrying mutations in PGI1, PGK1, GPM1, PYK1, and GCR1 where obtained by ethyl methane sulfonate (EMS) mutagenesis of S. cerevisiae (S. c.) X2180-1A (MATa SUC2 CUP1 gal2, from the Berkeley Yeast Stock Center). 35,000 independent colonies were grown on YEP-3% glycerol-2% ethanol and were screened by replica plating for the inability to grow on YEP-4% dextrose (Table 1).

Identification of specific lesions was made by complementation tests with known glycolysis mutants (Ciriacy and Breitenbach (1979) J.Bacteriol. 139:152-60), while at least 15 additional complementation groups were found by intercrossing mutant strains. Enzyme assays (Clifton et al. (1980) Genetics 88:1-11) confirmed the glycolytic defects in pgi1, pgk1, gpm1, pyk1, and gcr1 mutants.

A LEU2 mutant was also derived from S. cerevisiae X2180-1A by EMS treatment and was crossed to X2180-1B (an isogenic MATα strain) to produce N501-1B (MATα leu2 SUC2 CUP1 gal2). Cycloheximide (cyh2) and canavanine (can1) resistances were then selected as spontaneous mutations in N501-1B. The glycolysis mutants were crossed to N501-1B to produce a series of isogenic leu2 strains each defective in a single glycolytic function or in GCR1.

A tpi1 mutant, S. cerevisiae GLU77 was crossed to N551-1A (MATa leu2 SUC2 CUP1 gal2); strains derived from this mating were crossed twice to N501-1B to produce a tpi1 leu2 strain, N587-2D, which was similar in genetic background to the other glycolysis mutants.

Mutations in three glucose phosphorylating enzymes produce a strain which is unable to grow on dextrose as the sole carbon source and which is resistant to catabolite repression by 2-deoxyglucose and glucosamine. N517-6C (hxk1 hxk2 glk1 leu2 can1-100 cyh2 ade2-1) was derived from a hxk1 hxk2 glk1 strains, D308.3, by screening for glucosamine-resistant spore colonies. Defects in glucose kinasing activities were confirmed by assay.

TABLE 1

Complementation Groups of glu⁻ Derivatives of X2180-1A

| Gene | No. of Mutants | |
|---|---|---|
| PYK1 | 14 | |
| PDC1 | 9 | |
| GCR1 | 4 | |
| PGI1 | 3 | |
| GPM1 | 3 | |
| PGK1 | 1 | |
| TPI1 | 0 | |
| FDP | 0 | |
| (LEU2) | (1) | |
| I | 11 | 60 other mutations not in the complementation groups |
| II | 10 | |
| III | 3 | |
| IV | 5 | |
| V | 1 | |
| VI | 1 | |
| VII | 2 | |
| VIII | 3 | |
| IX | 2 | |
| X | 3 | |
| XI | 2 | |
| XII | 1 | |
| XIII | 1 | |
| XIV | 5 | |
| XV | 1 | |

27 sterile glu⁻ strains
35,000 colonies screened (EMS mutagenized for 50% kill)

The homothallic diploid strain, S. c. AB320 was the source of the yeast DNA pool (Nasmyth and Reed, Proc. Nat. Acad. Sci. (1980) 77:2119-2123 and was used as a control in some experiments.

The triose phosphate isomerase gene (including the upstream sequence having the regulatory signals) is as follows:

```
GAATCCATCAATAGATACGTCCTGAGGACCGTGCTACCCAAATGGACTGATTGTGAGGGA
-658          -650          -640          -630          -620          -610          -600

GACCTAACTACATAGTGTTTAAGATTACGGATATTTACTTACTTAGAATAATGCCATTT
     -590          -580          -570          -560          -550          -540

TTTGAGTTATAATCCTACGTTAGTGTGAGCGGGATTTAAACTGTGAGGACCTTAAT
     -530          -520          -510          -500          -490          -480

ACATTCAGACACTTCTGACGGTATCACCCTACTTATTCCCTTCGAGATTATCTAGGAA
     -470          -460          -450          -440          -430          -420

CCCATCAGGTTGGTGGAAGATTACCCGTTCTAAGACTTTTCAGCTTCCTCTATTGATGTT
     -410          -400          -390          -380          -370          -360

ACACTTGGACACCCCTTTCTGGCATCCAGTTTTTAATCTTCAGTGGCATGTGAGATTCT
     -350          -340          -330          -320          -310          -300

CCGAAATTAAAGCAATCACACAATTCTCTCGGATACCCTCGGTTGAAACTGACA
     -290          -280          -270          -260          -250          -240

GGTGGTTTGTTACGCATGCTAATGCAAAGGAGCCTATACCTTTGGCTCGGCTGCTGTA
     -230          -220          -210          -200          -190          -180

ACAGGGAATATAAAGGCAGCATAATTTAGGAGTTTAGTGAACTTGCAACATTTACTATT
     -170          -160          -150          -140          -130          -120

TTCCCTTCTTACGTAAATATTTCTTTAAATTCTATAACTACAAAAACAACATAAACTAAAAT
     -110          -100          -90           -80           -70           -60

MET
TTTGTATTCTTTTCTTGCTTAAATCTATAACTACAAAAACACATAAACTAAAAAT
     -50           -40           -30           -20           -10           -11

ALA ARG THR PHE PHE VAL GLY GLY ASN PHE LYS LEU ASN GLY SER LYS GLN SER ILE LYS
GCTAGAACTTTCTTTGTCGGTGGTAACTTTAAATTAAACGGTTCCAAACAATCCATTAAA
              10            20            30            40            50            60

GLU ILE VAL GLU ARG LEU ASN THR ALA SER ILE PRO GLU ASN VAL GLU VAL ILE CYS
GGAAATTGTTGAAAGATTGAACACTGCTTCTATCCCAGAAAATGTCGAAGTTGTTATCTG
              70            80            90            100           110           120

PRO PRO ALA THR TYR LEU ASP TYR SER VAL SER LEU VAL LYS LYS PRO GLN VAL THR VAL
TCCTCCAGCTACTTACTTAGACTACTCTGTCTCTTTGGTTAAGAAGCCACAAGTCACTGT
              130           140           150           160           170           180

GLY ALA GLN ASN ALA TYR LEU LYS ALA SER GLY ALA PHE THR GLY GLU ASN SER VAL ASP
CGGTGCTCAAAACGCCTACTTGAAGGCTTCTGGTGCTTTCACCGGTGAAAACTCCGTTGA
              190           200           210           220           230           240
```

-continued

```
GLN  ILE  LYS  ASP  VAL  GLY  ALA  LYS  TRP  VAL  ILE  LEU  GLY  HIS  SER  GLU  ARG  ARG  SER  TYR
CCA  AAT  CAA  GGA  TGT  TGG  CTA  AAG  TGG  GTT  ATT  TTG  GGT  CAC  TCC  GAA  AAG  ATC  TTA
   250              260              270              280              290              300

PHE  HIS  GLU  ASP  ASP  LYS  PHE  ILE  ALA  ASP  LYS  THR  LYS  PHE  ALA  LEU  GLY  GLN  GLY  VAL
CTT  CCA  CGA  AGA  TGA  CAA  GTT  CAT  TGC  TGA  CAA  GAC  CAA  GTT  CGC  TTT  AGG  TCA  AGG  TGT
   310              320              330              340              350              360

GLY  VAL  ILE  LEU  CYS  ILE  GLY  GLU  THR  LEU  GLU  GLU  LYS  LYS  ALA  GLY  LYS  THR  LEU  ASP
CGG  TGT  CAT  CTT  GTG  TAT  CGG  TGA  AAC  TTT  GGA  AGA  AAA  GAA  AGG  CCG  GTA  AGA  CTT  TGG  A
   370              380              390              400              410              420

VAL  VAL  GLU  ARG  GLN  LEU  ASN  ALA  VAL  LEU  GLU  GLU  VAL  LYS  ASP  TRP  THR  ASN  VAL  VAL
TGT  TGT  TGA  AAG  ACA  ATT  GAA  CGC  TGT  CTT  GGA  AGA  AGT  TAA  GGA  CTG  GAC  TAA  CGT  CGT
   430              440              450              460              470              480

VAL  ALA  TYR  GLU  PRO  VAL  TRP  ALA  ILE  GLY  THR  GLY  LEU  ALA  ALA  THR  PRO  GLU  ASP  ALA
TGT  CGC  TTA  CGA  ACC  AGT  CTG  GGC  CAT  TGG  TAC  CGG  TTT  GGC  TGC  TAC  TCC  AGA  AGA  TGC
   490              500              510              520              530              540

GLN  ASP  ILE  HIS  ALA  SER  ILE  ARG  LYS  PHE  LEU  ALA  SER  LYS  LEU  GLY  ASP  LYS  ALA  ALA
CAG  GAT  ATT  CAC  GCT  TCC  ATC  AGA  AAG  TTC  TTG  GCT  TCC  AAG  TTG  GGT  GAC  AAG  GCT  GC
   550              560              570              580              590              600

SER  GLU  LEU  ARG  ILE  LEU  TYR  GLY  GLY  SER  ALA  ASN  GLY  SER  ASN  ALA  VAL  THR  PHE  LYS
CAG  CGA  ATT  GAG  AAT  CTT  ATA  CGG  TGG  TTC  CGC  TAA  CGG  TAG  CAA  CGC  CGT  TAC  CTT  CAA
   610              620              630              640              650              660

ASP  LYS  ALA  ASP  VAL  ASP  GLY  PHE  LEU  VAL  GLY  GLY  ALA  SER  LEU  LYS  PRO  GLU  PHE  VAL
GGA  CAA  GGC  TGA  TGT  CGA  TGG  TTT  CTT  GGT  CGG  TGG  TGC  TTC  TTT  GAA  GCC  AGA  ATT  TGT
   670              680              690              700              710              720

ASP  ILE  ILE  ASN  SER  ARG  ASN  ***
TGA  TAT  CAT  CAA  CTC  TAG  AAA  CTA  AGA  TTA  ATA  AAT  TAT  ATA  AAA  ATA  TTA  TCT  TCT  TTT
   730              740   747 +1            +10              +20              +30

TCT  TTA  TCT  AGT  GTT  ATG  TAA  AAA  TAA  AAT  TGA  TGA  CTA  CGG  AAA  GCT  TTT  TTA  TAT  TGT
    +40              +50              +60              +70              +80              +90

TTC  TTT  TTC  ATT  CTG  AGC  CAC  TTA  AAT  TTC  GTG  AAT  GTT  CTT  GTA  AGG  GAG  CGT  AGA  TTT
   +100             +110             +120             +130             +140             +150

ACA  AGT  GAT  ACA  ACA  AAA  AAG  CAA  GGC  GCT  TTT  TCT  AAT  AAA  AAG  AAA  AAG  CAT  TTA  AC
   +160             +170             +180             +190             +200             +210

AAT  TGA  ACA  CCT  CTA  TAT  CAA  CAG  AAG  A
   +220             +230             +240
```

The pyruvate kinase gene upstream sequence having the regulatory signals is as follows:

| 10 | 20 | 30 | 40 | 50 | 60 |
|---|---|---|---|---|---|
| GAATTCAGCA | TGATAGCTAC | GTAAATGTGT | TCCGCACCGT | CACAAAGTGT | TTTCTACTGT |
| CTTAAGTCGT | ACTATCGATG | CATTTACACA | AGGCGTGGCA | GTGTTTCACA | AAACATGACA |
| 70 | 80 | 90 | 100 | 110 | 120 |
| TCTTTCTTCT | TTCGTTCATT | CAGTTGAGTT | GAGTGAGTGC | TTTGTTCAAT | GGATCTTAGC |
| AGAAAGAAGA | AAGCAAGTAA | GTCAACTCAA | CTCACTCACG | AAACAAGTTA | CCTAGAATCG |
| 130 | 140 | 150 | 160 | 170 | 180 |
| TAAAATGCAT | ATTTTTTCTC | TTGGTAAATG | AATGCTTGTG | ATGTCTTCCA | AGTGATTTCC |
| ATTTTACGTA | TAAAAAAGAG | AACCATTTAC | TTACGAACAC | TACAGAAGGT | TCACTAAAGG |
| 190 | 200 | 210 | 220 | 230 | 240 |
| TTTCCTTCCC | ATATGATGCT | AGGTACCTTT | AGTGTCTTCC | TAAAAAAAAA | AAAAGGCTCG |
| AAAGGAAGGG | TATACTACGA | TCCATGGAAA | TCACAGAAGG | ATTTTTTTTT | TTTTCCGAGC |
| 250 | 260 | 270 | 280 | 290 | 300 |
| CCATCAAAAC | GATATTCGTT | GGCTTTTTTT | TCTGAATTAT | AAATACTCTT | TGGTAACTTT |
| GGTAGTTTTG | CTATAAGCAA | CCGAAAAAAA | AGACTTAATA | TTTATGAAA | ACCATTGAAA |
| 310 | 320 | 330 | 340 | 350 | 360 |
| TCATTTCCAA | GAACCTACTTT | TTTCCAGTTA | TATCATGGTC | CCCTTTCAAA | GTTATTCTCT |
| AGTAAAGGTT | CTTGGAGAAA | AAAGGTCAAT | ATAGTACCAG | GGGAAAGTTT | CAATAAGAGA |
| 370 | 380 | 390 | 400 | 410 | 420 |
| ACTCTTTTTC | ATATTCATTC | TTTTTCATCC | TTTGGTTTTT | TATTCTTAAC | TTGTTTATTA |
| TGAGAAAAAG | TATAAGTAAG | AAAAAGTAGG | AAACCAAAAA | ATAAGAATTG | AACAAATAAT |
| 430 | 440 | 450 | 460 | 470 | 480 |
| TTCTCTCTTG | TTTTCTATTTA | CAAGACACCA | ATCAAAACAA | ATAAAACATC | ATCACAATGT |
| AAGAGAGAAC | AAAGATAAAT | GTTCTGTGGT | TAGTTTTGTT | TATTTTGTAG | TAGTGTTACA |
| 490 | 500 | 510 | 520 | 530 | 540 |
| CTAGATTAGA | AAGATTGACC | TCATTAAACG | TTGTTGCTGG | TTCTGACTTG | AGAAGAACCT |
| GATCTAATCT | TTCTAACTGG | AGTAATTTGC | AACAACGACC | AAGACTGAAC | TCTTCTTGGA |
| 550 | 560 | 570 | 580 | 590 | 600 |
| CCATCATTGG | TACCATCGGT | TCAAAGACCA | ACAACCCAGA | AACCTTGGTT | GCTTTGAGAA |
| GGTAGTAACC | ATGGTAGCCA | AGTTTCTGGT | TGTTGGGTCT | TTGGAACCAA | CGAAACTCTT |
| 610 | 620 | 630 | 640 | 650 | 660 |
| AGGCTGGTTT | GAACATTGTT | CGTATGAACT | TCTCTCACGG | TTCTTACGAA | TACCACAAGT |
| TCCGACCAAA | CTTGTAACAA | GCATACTTGA | AGAGAGTGCC | AACAATGCTT | ATGGTGTTCA |
| 670 | 680 | 690 | 700 | | |
| CTGTCGTTGA | CAACGCCAGA | AAGTCCGAAG | AATTGTACCC | | |
| GACAGCAACT | GTTGCGGTCT | TTCAGGCTTC | TTAACATGGG | | |

Screening of clone bank.

The leu2 glycolysis mutants were transformed with a yeast DNA pool inserted into pYE13, a high copy plasmid carrying a selectable LEU2 wild-type gene (Broach et al., Gene (1979) 8:121-133). The glycolytic genes were obtained by complementation, involving the simultaneous selection for growth on glucose and leucine prototrophy. A synthetic medium containing yeast nitrogen base, 4% glucose, and the following supplements was used: per liter, 40 mg adenine, 20 mg arginine, 50 mg aspartate, 10 mg histidine, 60 mg isoleucine, 40 mg lysine, 10 mg methionine, 60 mg phenylalanine, 50 mg threonine, 40 mg tryptophan, 50 mg tyrosine, 20 mg uracil, and 60 mg valine.

The transformants were purified on leucineless media and were then grown on a non-selective medium (YEPGE) to allow mitotic segregation of the plasmids. Strains which cosegregated the leu2 and glycolysis mutant phenotypes, as determined by replica plating on selective media, were assayed for glycolytic enzyme activities. Yeast DNA preps were made, and the E. coli strain, RR1, was transformed, selecting for ampicillin resistance, to verify the presence of plasmid DNAs in these yeast glycolytic transformants.

Enzyme Assays.

The transformed yeast strains were selectively grown on minimal medium with 8% glucose (adenine was added to a final concentration of 50 mg/l). The wild-type control, N501-1B, was grown on the same medium plus leucine (100 mg/l). The glycolysis mutant strains were grown on YEP-5% glycerol-1% lactate. Overnight cultures were fed fresh media and were aerobically grown at 30° for four hours before harvesting. The cells were washed two times with water and resuspended in 50mM $K_2HPO_4$ 2mM EDTA 3mM 2-mercaptoethanol (adjusted to pH 7.4 with HCl). Extracts were obtained by vortexing the cells with an equal volume of glass beads (0.45 mm diam.) at high speed for two minutes. The cell debris was removed by centrifugation in a microfuge for 15 min. at 4°. Enzymes were assayed as described by Clifton and Breitenbach, supra. Protein concentrations were determined by the Biuret-TCA method.

In order to determine the activity of the various glycolytic genes in the transformants, the various enzymes were assayed and the results for the transformants were compared to mutant and wild-type strains. The gcr1 mutant had 5-10% of the wild-type levels of most glycolytic activities (exemplified by PGI, aldolase and enolase) and grows very poorly on glucose media. In contrast, the GCR1 transformants had nearly wild-type levels of enzymes and were virtually identical to wild-type for growth on glucose media. The other glycolysis mutants had less than 5% of the normal levels of their respective enzyme activities. However, when transformed with a complementing high copy plasmid, the specific enzyme activities were substantially elevated above wild-type levels (typically 5–10 fold higher). The following Table 2 indicates the results.

TABLE 2

Comparison of Glycolytic Activities in Wild-type, Mutant, and Transformed Strains

| Enzyme | Activities | | | Ratio: Transf/Wt |
|---|---|---|---|---|
| | Wild-type[a] | Mutant[b] | Transformant[c] | |
| PGI | 2.85 | .0065 | 31.49 (10) | 11.1 |
| TPI | 18.3 | .0000 | 167.8 (10) | 9.2 |
| PGK | 1.99 | .0046 | 17.67 (3) | 8.9 |
| GPM | 0.74 | .0000 | 4.80 (10) | 6.5 |
| PYK | 4.02 | .0057 | 14.77 (10) | 3.7 |

| | Wild-type[a] | gcr1 Mutant[d] | GCR1 Transf[c] | |
|---|---|---|---|---|
| PGI | 2.85 | .2436 | 2.42 (10) | .85 |
| Aldolase | 4.33 | .4415 | 2.96 (10) | .68 |
| Enolase | 0.43 | .0274 | .316 (10) | .74 |

[a]Wild-type is N501-1B.
[b]The respective mutant strains are N543-9D (pgi1 leu2), N587-2D (tpi1 leu2), N548-8A (pkg1 leu2), N583-2C (gpm1 leu2), and N549-3A (pyk1 leu2).
[c]The activities of the transformants are averages for many different isolates. The numbers in parentheses represent the numbers pf independent transformants assayed.
[d]The gcr1 leu2 mutant strain is N525-2C.

In order to demonstrate that the hyperproduction of glycolytic enzymes was specific to the mutational defect complemented by the particular plasmid, assays for ten different glycolytic proteins were conducted on the various transformants. The following Table 3 reports the results for one transformant for each of the six different glycolysis genes which were examined in detail.

TABLE 3

RELATIVE ENZYME ACTIVITIES OF WILD-TYPE AND TRANSFORMED STRAINS
GLYCOLYTIC ENZYMES

| Strains | GLK | PGI | PFK | FBA | TPI | GLD | PGK | GPM | ENO | PYK |
|---|---|---|---|---|---|---|---|---|---|---|
| N501-1B | 1.00 | 1.00 | 1.00 | 1.00 | 1.00 | 1.00 | 1.00 | 1.00 | 1.00 | 1.00 |
| Transformant GCR-8 | 1.05 | 0.63 | 1.44 | 0.79 | 0.62 | 0.63 | 0.75 | 0.56 | 0.51 | 1.36 |
| Transformant PGI-19 | 0.64 | 5.63 | 1.26 | 0.57 | 0.58 | 0.75 | 0.51 | 0.32 | 0.54 | 0.82 |
| Transformant TPI-10 | 0.99 | 0.77 | 1.35 | 0.99 | 13.85 | 0.87 | 0.64 | 1.01 | 0.64 | 1.14 |
| Transformant PGK-2 | 0.54 | 0.45 | 1.05 | 0.54 | 0.46 | 0.63 | 2.99 | 0.24 | 0.43 | 0.83 |
| Transformant GPM-2 | 0.97 | 0.82 | 1.69 | 1.02 | 1.02 | 0.85 | 0.97 | 12.75 | 0.72 | 2.00 |
| Transformant PYK-1 | 1.02 | 0.83 | 1.09 | 0.89 | 1.22 | 0.84 | 1.23 | 0.49 | 0.85 | 6.53 |

The GCR-8 transformant gave nearly wild-type levels of all ten enzymes, while PGI-19, TPI-10, PGK-2, GPM-2 and PYK-1 transformants overproduced their respective glycolytic proteins, but not other enzymes.

It was noted that the plasmids readily segregated (typically 5–50% segregation in fully grown cultures even under selective pressure of leucine prototrophy, so the assayed cultures probably contain cells with a range of number of plasmids. By complementation in E. coli and/or sequencing, TPI1 and PYK1 have both been shown to be the structural gene.

Exploitation of the promoter for TPI1 for the production of human $\alpha_1$-antitrypsin was demonstrated as follows. The plasmid CV13 was employed. CV13 can be maintained by selection of yeast with an average of about ten copies per cell. CV13 is comprised of pBR322, the replicon for the 2$\mu$-plasmid and the yeast LEU2 gene. TPI1 promoter fragment was obtained by cutting the TPI1 gene at the unique KpnI site (bases 511 to 518); and the resulting linearized DNA was then treated with Ba131 for four to five minutes in order to remove the TPI1 structural sequences. Linkers, either EcoRI, Hind III or BamHI, were then inserted. The linkers will then cleave with the appropriate restriction enzyme to provide cohesive ends for insertion of human $\alpha_1$-antitrypsin genes. The human $\alpha_1$-antitrypsin gene was digested with BamHI, which cleaves at the 5'-terminus of the coding strand to remove the information for a single glutamic acid codon from the mature protein. Four different constructions were prepared, as set forth in the following Table 4. From this table it is noted that the glutamic acid codon is substituted by the codons for alanine and proline in three of the constructions having the initiator methionine.

After ligation of the human $\alpha_1$-AT construction into the CV13 plasmid, the resulting plasmid was transformed into S. c. N501-1B. The resulting yeast cells were then grown on a minimal synthetic medium.

TABLE 4

| Plasmid | N—terminal amino acid | Orientation in CV13 |
|---|---|---|
| CAT1 | met glu + hAT* | clockwise |
| C-T$\alpha$2 | met ala pro + hAT | counterclockwise |
| C-T$\alpha$1 | met ala pro + hAT | clockwise |
| C-TS$\alpha$2 | met ala pro + hAT, but missing part of TPI promoter | counterclockwise |

*remainder of approximately 400 amino acids of human $\alpha_1$-antitrypsin

Yeast cells containing the human $\alpha_1$-AT genes were broken open by vortexing with glass beads (0.45mm) at high speed for 2–3 minutes. The extraction buffer contained 50mM $K_2HPO_4$, 2mM EDTA, 2mM 2-mercaptoethanol and 1 mM PMSF (pH7.4) cell debris was removed by centrifugation and the extracts contain 3–4mg/ml protein as determined by Lowry assays.

The presence of human $\alpha_1$-antitrypsin was determined using a RIA, employing tritium-labeled human $\alpha_1$-AT and antibody directed against the protein. The following Table 5 indicates the results.

TABLE 5

| | Competition assay for alpha-1 antitrypsin | | | | |
|---|---|---|---|---|---|
| Plasmid | Tritium Counts | Average Count | $\alpha_1$-AT [$\mu$g] | Total Protein ($\mu$g) | % Total Protein |
| CAT1 | 46010 52257 | 49133.5 | 0.75 | 420 | .18 |
| C−T$\alpha$2 | 12268 13330 | 12799 | 3.35 | 380 | .88 |
| C+T$\alpha$1 | 41635 39071 | 40353 | 0.95 | 360 | .26 |
| C−TS$\alpha$2 | 66490 70038 | 68264 | 0 | 345 | 0 |
| Controls** | | | | Counts | |
| 0 $\mu$g $\alpha$-1 | | | | 68440 | |

TABLE 5-continued

| Competition assay for alpha-1 antitrypsin | |
| --- | --- |
| 0.25 μg α-1 | 65333 |
| 0.5 μg α-1 | 58928 |
| 1.0 μg α-1 | 38468 |
| 2.0 μg α-1 | 19559 |
| 3.0 μg α-1 | 14432 |
| 4.0 μg α-1 | 11155 |
| 5.0 μg α-1 | 9615 |

*Plasmids were grown in yeast strain, N501-1B. 100 μl of extracts were assayed.
**Non-radioactive alpha-1 antitypsin mixed with 100 μl of yeast extract (330 μg protein)

It is evident from the above results that an immunologically active product is obtained, which is capable of competing with naturally occurring human $\alpha_1$-AT for antibodies to the native protein. Furthermore, the expression of the $\alpha_1$-AT gene is regulated by the TPI promoter, for as is seen, where a portion of the TPI promoter is removed, no $\alpha_1$-AT is produced. In addition, the production of the mammalian protein human $\alpha_1$-AT has not been optimized in the above study, so that the results indicate a minimum production of product which can be further enhanced. Thus, the TPI promoter is found to be an effective promoter for efficiently producing high yields of expression products of alien DNA.

It is evident from the above results that yeast promoters can be efficiently used for the production of foreign proteins by regulating the expression of alien DNA in yeast. The promoters are found to be strong promoters, so as to provide for a high degree of expression. Furthermore, it would appear that the messengers are sufficiently stable as to allow for a significant degree of translation into the desired expression product. Furthermore, by employing the glycolytic promoters and appropriate nutrient media, the expression of the alien DNA can be modulated. In this way, production of the alien DNA can be turned on and off. Thus, the subject invention provides a method for using yeast as efficient host in the production of foreign proteins, where the production may be modulated. In addition, by using the glycolytic regulation gene, one can turn on and off a plurality of glycolytic promoters.

Although the foregoing invention has been described in some detail by way of illustration and example for purposes of clarity of understanding, it will be obvious that certain changes and modification may be practiced within the scope of the appended claims.

What is claimed is:

1. A DNA expression vector capable of replication in Saccharomyces cerevisiae and containing a Saccharomyces cerevisiae promoter which regulates the transcription of a glycolytic protein, which protein is triose phosphate isomerase or pyruvate kinase, said Saccharomyces cerevisiae followed downstream by a gene, under the regulation of said promoter, expressing a protein other than the glycolytic protein normally regulated by such promoter.

2. A DNA expression vector according to claim 1, having a marker for selection in a Saccharomyces cerevisiae.

3. A DNA expression vector according to claim 1, having a gene expressing a foreign protein downstream from said promoter and under the regulation of said promoter.

4. A DNA expression vector according to claim 1, wherein said promoter is followed by a gene expressing protease inhibitor having substantially the same structure as $\alpha_1$-antitrypsin.

5. A DNA expression vector according to any of claims 1, 2, 3 or 4, wherein said promoter is the triose phosphate isomerase promoter.

6. A DNA expression vector according to claim 5, wherein a gene expressing an enzyme in a metabolic pathway of said Saccharomyces cerevisiae is present.

7. A DNA expression vector according to any of claims 1, 2, 3 or 4, wherein said promoter is the pyruvate kinase promoter.

8. A DNA expression vector according to claim 7, wherein a gene expressing an enzyme in a metabolic pathway of said Saccharomyces cerevisiae is present.

9. A Saccharomyces cerevisiae cell containing an extrachromosomal element according to any of claims 1, 2, 3 or 4.

10. A DNA expression vector comprising a Saccharomyces cerevisiae triose phosphate isomerase promoter followed by a gene expressing a foreign protein under the regulation of said promoter.

11. A DNA expression vector according to claim 10, wherein said foreign protein is a protein having protease inhibition activity.

12. A DNA expression vector according to claim 11, wherein the major sequence of said protein is the same sequence as human $\alpha_1$-antitrypsin.

13. A DNA expression vector comprising a Saccharomyces cerevisiae pyruvate kinase promoter followed by a gene expressing a foreign protein under regulation of said protein.

14. A method for preparing any foreign protein which comprises:
introducing into Saccharomyces cervisiae, a DNA expression vector according to claims 1, 2, 3, or 4; and
growing said Saccharomyces cervisiae in an appropriate medium and isolating the protein expressed by said foreign DNA.

15. A Saccharomyces cerevisiae said promoter and said gene integrated into its genome from a DNA expression vector according to any of claims 1, 2, 3 or 4.

16. A Saccharomyces cervisiae cell according to claim 15, wherein said promoter is the triose phosphate isomerase promoter.

17. A Saccharomyces cerevisiae cell according to claim 15, wherein said promoter is the pyruvate kinase promoter.

* * * * *

UNITED STATES PATENT AND TRADEMARK OFFICE
CERTIFICATE OF CORRECTION

PATENT NO. : 4,599,311
DATED : July 8, 1986
INVENTOR(S) : Kawasaki

It is certified that error appears in the above—identified patent and that said Letters Patent is hereby corrected as shown below:

In column 4, line 36, delete the word "metal" and insert the word "metals" therefor.

In column 12, line 3, delete the expression "LEU2" and insert the expression --leu2-- therefor; in line 23, delete the word "strains" and insert the word --strain-- therefor.

In column 19, line 27, delete the expression "pkgl" and insert --pgkl-- therefor.

In column 20, in Table 5, in line 63, delete "+" and insert -- - -- therefor.

Signed and Sealed this

Fifteenth Day of September, 1987

Attest:

DONALD J. QUIGG

Attesting Officer      Commissioner of Patents and Trademarks